United States Patent [19]

Makino et al.

[11] Patent Number: 5,393,493
[45] Date of Patent: Feb. 28, 1995

[54] ANALYTICAL ELEMENT FOR WHOLE BLOOD

[75] Inventors: Yoshihiko Makino; Kaoru Terashima; Toru Kitani; Naofumi Hora, all of Saitama, Japan

[73] Assignee: Fuji Photo Film Co., Ltd., Kanagawa, Japan

[21] Appl. No.: 993,459

[22] Filed: Dec. 15, 1992

Related U.S. Application Data

[63] Continuation of Ser. No. 833,807, Feb. 10, 1992, abandoned, which is a continuation of Ser. No. 476,955, Feb. 8, 1990, abandoned.

[30] Foreign Application Priority Data

Feb. 9, 1989 [JP] Japan ................................... 1-30408
Mar. 30, 1989 [JP] Japan ................................... 1-80108

[51] Int. Cl.$^6$ ....................... G01N 33/52; G01N 21/78
[52] U.S. Cl. ........................................... 422/56; 422/57; 436/170
[58] Field of Search ..................... 422/56, 57, 60; 436/170

[56] References Cited

U.S. PATENT DOCUMENTS

| | | | |
|---|---|---|---|
| H000,623 | 4/1989 | Miyazako | 422/57 X |
| 3,992,158 | 11/1976 | Przybylowicz et al. | 435/11 X |
| 4,042,335 | 8/1977 | Clement | 435/13 X |
| 4,089,747 | 5/1978 | Bruschi | 435/11 X |
| 4,256,693 | 3/1981 | Kondo et al. | 422/56 |
| 4,292,272 | 9/1981 | Kitajima et al. | 422/57 |
| 4,557,901 | 12/1985 | Koyama et al. | 422/57 X |
| 4,578,245 | 3/1986 | Arai et al. | 422/86 X |
| 4,594,224 | 6/1986 | Okaniwa et al. | 422/57 X |
| 4,613,567 | 9/1986 | Yasoshima et al. | 422/57 X |
| 4,788,153 | 11/1988 | Detwiler | 422/57 X |
| 4,919,890 | 4/1990 | Arai et al. | 422/57 X |
| 4,939,085 | 7/1990 | Arai | 422/57 X |
| 4,959,305 | 9/1990 | Woodrum | 422/57 X |
| 4,966,856 | 10/1990 | Ito et al. | 422/57 X |
| 4,975,366 | 12/1990 | Sudo et al. | 422/56 X |

Primary Examiner—James C. Housel
Assistant Examiner—Arlen Soderquist
Attorney, Agent, or Firm—McAulay, Fisher, Nissen & Goldberg

[57] ABSTRACT

An integral multilayer analytical element in which a first fibrous porous layer, a nonfibrous porous layer, and a second fibrous porous layer superposed in this order on a water-impermeable light-transmissive support the first fibrous porous-layer having a larger pore size than the nonfibrous porous layer. The above three porous layers are integrally laminated to each other substantially closely by an adhesive discontinuously disposed so as to form microspaces continuing through from one layer to the next so as not to interfere with the approximately uniform permeation of liquid. A reagent composition which produces an optically detectable change in the presence of an analyte is incorporated in at least one of said three porous layers. When a nonporous reagent layer is incorporated on the support in the above analytical element, the reagent composition is incorporated in the nonporous reagent layer. By using the analytical element of the invention, the analytical values of various analytes of blood samples can be obtained independently of hematocrit values from whole blood samples and blood plasma samples in the range of the hematocrit values of 0% to 55%.

5 Claims, 2 Drawing Sheets

ANALYTICAL ELEMENT FOR WHOLE BLOOD

This is a continuation of application Ser. No. 07/833,807, filed Feb. 10, 1992, which in turn is a continuation of Ser. No. 07/476,955, filed Feb. 8, 1990, both now abandoned.

BACKGROUND OF THE INVENTION

1. Field of the Invention

This invention relates to a dry-type chemical analytical element used for determination of a particular substance in a body fluid, such as blood.

2. Description of the Prior Art

The quantitative analyses of various metabolic components, such as glucose, bilirubin, urea nitrogen, uric acid, cholesterol, lactate dehydrogenase, creatine kinase, ALT (Alanine aminotransferase) and AST (Aspartate aminotransferase), are important in clinical analysis, particularly in the diagnosis of diseases, the follow-up of the course of treatment, the judgement of prognosis and the like. In clinical assays, where the sample is blood or the like, it is preferable that a highly accurate assay be conducted by using a minute amount of liquid sample. In the past, wet methods using a solution of reagent were widely utilized, however they were poor in rapidity.

On the other hand, dry methods are also known such as clinical assay means. The dry method uses an analytical element, such as, a test piece or a multilayer analytical element, in a substantially dry state where an analytical reagent system is incorporated. The dry methods are superior to the wet methods in terms of simplicity of operation, rapidity, cost, etc. Dry-type multilayer analytical elements have been developed as rapid and accurate assay means, and they are disclosed in U.S. Pat. Nos. 3,992,158, and 4,292,272, EP 0 162 302A, etc. The dry-type multilayer analytical element is, for example, composed of a transparent support, a reagent layer, a light-reflecting layer, a spreading layer, and the like. The transparent support is a subbed thin plastic film or the like. The reagent layer is coated on the support, and contains the reagent which reacts with the analyte in a liquid sample to develop a color, the optical density of which is proportional to the amount of the analyte. The light-reflecting layer functions to block the light incident into the reagent layer so that it does not reach the spreading layer, and to minimize the influence of the liquid sample spotted on the spreading layer at the time of measuring the optical density of the reagent layer. The spreading layer uniformly spreads the liquid sample spotted thereon to an area in proportion to the liquid amount. When quantitative analysis is carried out using the dry-type analytical element, a definite amount of a liquid sample, such as, a whole blood sample is spotted on the spreading layer. The liquid sample spreads in the spreading layer, and passes through the light-reflecting layer. The sample reaches the reagent layer, and reacts with the reagent to form color. After the spotting, the analytical element is incubated for a suitable time at a constant temperature to allow the color reaction to proceed sufficiently. Light is irradiated onto the reagent layer from the side of the transparent support, and reflection optical density is measured at a particular wave length region. The amount of the analyte is determined by using a calibration curve obtained previously.

In the past, the sample to be analyzed was usually blood serum or blood plasma where the erythrocytes were removed, irrespective of whether the wet or dry method was used. However, since the separation of erythrocytes requires labor and equipment cost, analysis is preferably carried out using undiluted whole blood.

When whole blood is analyzed by the dry method, blood cells, i.e. erythrocytes and leukocytes, and other macromolecular components should be separated in the analytical element by some means. For example, the analytical element disclosed in U.S. Pat. No. 3,992,158 is provided with a filtering layer for separating blood cells and other macromolecular components. However, the filtering layer requires a lot of time for the removal of blood cells. Moreover, a part of the analyte is lost in the filtering layer, and thereby, the analysis becomes inaccurate.

Another dry-type analytical element utilizable for the analysis of a particular component in whole blood is disclosed in EP 0 226 465A. In the analytical element, erythrocytes in a whole blood sample are separated from plasma in order to remove the interference of the erythrocytes, and moreover, the analyte in the plasma rapidly diffuses into the reagent layer. The analytical element is composed of a first nonfibrous porous layer, a second nonfibrous porous layer and a fibrous porous layer. They are intergrally and substantially closely laminated in this order each through an adhesive discontinuously disposed so as to form microspaces continuing through from one layer to the next so as not to interfere with the approximately uniform permeation of liquid. The color forming reagent composition is incorporated into any one of the above three porous layers, and the mean effective pore size of the second nonfibrous porous layer is in the range of 0.8 to 30 $\mu$m. However, when whole blood samples were analyzed by using the above analytical element, the analytical results among the blood samples having the same analyte content varied considerably depending on the hematocrit values (the volume per cent of blood cells in blood).

SUMMARY OF THE INVENTION

An object of the invention is to provide a dry-type analytical element capable of separating erythrocytes in whole blood to avoid their interference with the analytical element, capable of diffusing the analyte in the blood plasma into the reagent layer rapidly, and capable of determing the amount or the activity value of the analyte with high accuracy irrespective of the hematocrit value of the whole blood sample.

Such an object has been achieved by an integral multilayer analytical element which comprises a first fibrous porous layer, a nonfibrous porous layer, and a second fibrous porous layer superposed in this order onto a water-impermeable light-transmissive support. The above three porous layers are integrally laminated to each other substantially closely by an adhesive discontinuously disposed so as to form microspaces continuing through from one layer to the next so as not to interfere with the approximately uniform permeation of liquid. A reagent composition which produces an optically detectable change in the presence of an analyte is incorporated into at least one of said three porous layers. On the other hand, when a nonporous reagent layer is incorporated on the support in the above analytical element, the reagent composition is incorporated into the nonporous reagent layer.

DETAILED DESCRIPTION OF THE INVENTION

Figure 1:
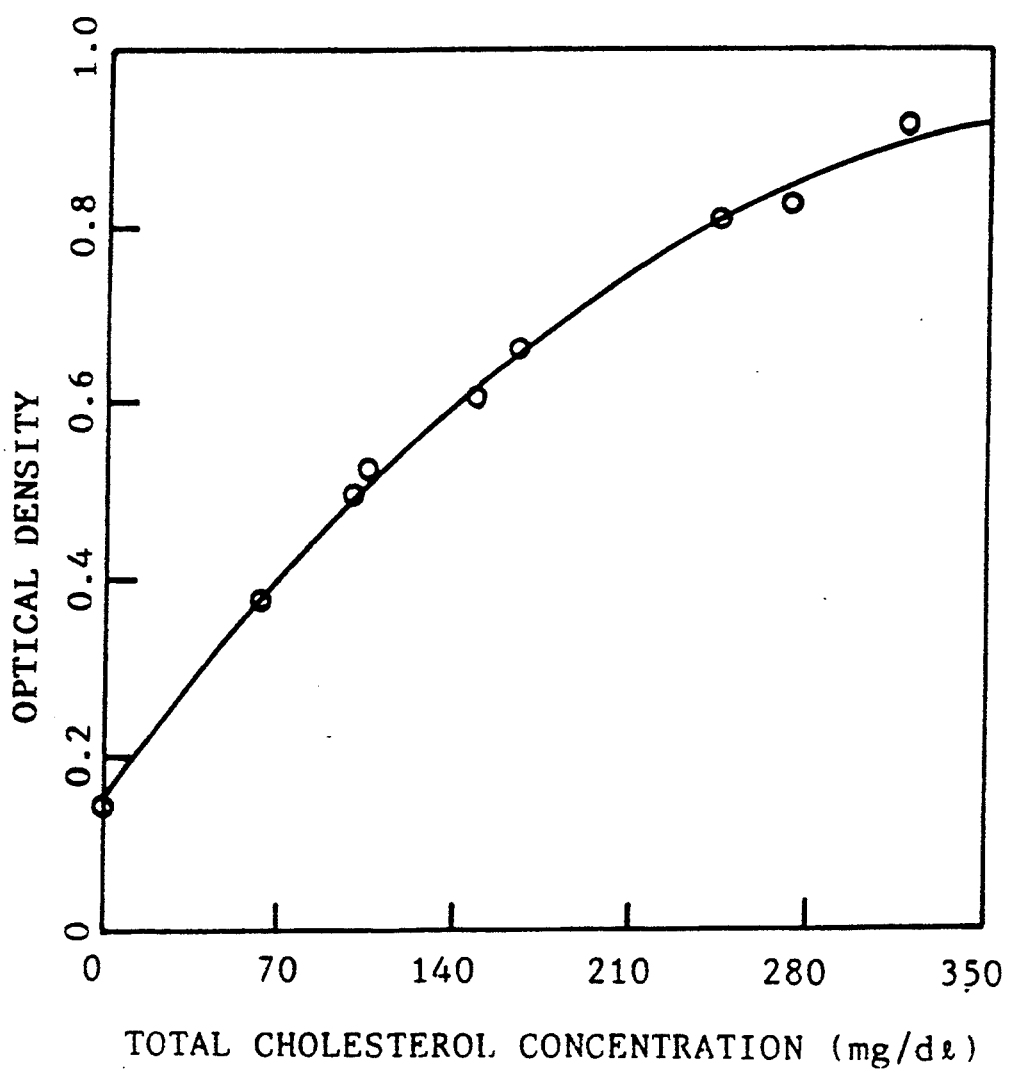
FIG. 1 is a graph indicating a relationship between the total cholesterol concentration of samples and a reflection optical density of multilayer analytical elements.

The nonfibrous porous layer is preferably a blushed polymer layer composed of a cellulose ester, such as, cellulose acetate, cellulose acetate/butyrate or cellulose nitrate, disclosed in U.S. Pat. Nos. 3,992,158 or 1,421,341. It may be a microporous membrane of polyamide, such as, 6-nylon or 6,6-nylon, or polyethylene, polypropylene, or the like, or may be a microporous membrane composed of the polysulfone disclosed in Japanese Patent KOKAI 27006/1987. In addition, it may also be a continuous microspace-containing porous layer where polymer particulates, glass particulates, diatomaceous earth or the like are joined by a hydrophilic or non-water-absorptive polymer, such as disclosed in U.S. Pat. Nos. 3,992,158, and 4,258,001.

The effective pore size of the nonfibrous porous layer is preferably 0.8 to 30 $\mu$m as measured by the bubble point method based upon ASTM F316-70. In the case that the nonfibrous porous layer is a membrane filter composed of a blushed polymer prepared by the phase separation method, liquid paths in the direction of thickness are, in general, the narrowest at the free side surface at the time of the production of the membrane (glossy surface), and the pore size, assuming that the cross section of the liquid path is a circle, is the smallest in the vicinity of the free surface. The pore sizes of the individual liquid paths estimated at the narrowest part along the path with respect to the direction of thickness have a distribution in the direction of the membrane surface, and the maximum value among the varying pore sizes controls the filtration ability for particles. It is usually measured by the bubble point method and is defined as the effective pore size herein.

In the case of using a membrane filter composed of blushed polymer prepared by the phase separation method, it is preferable that the glossy face is disposed on the support side, that is, on the side facing the first nonfibrous porous layer.

The material constituting the fibrous porous layer may be filter paper, nonwoven fabric, woven fabrics, such as plain weaves, knitted fabrics, such as tricot fabric, glass fiber filter paper, etc. Preferable materials for the fibrous porous layer are woven fabrics and knitted fabrics. The woven fabric, etc., may be treated with a glow discharge, such as disclosed in GB 2 087 074A.

The nonfibrous porous layer is laminated to the first fibrous porous layer by an adhesive. The adhesive is disposed partially or discontinuously so as to form through microspaces so as not to interfere with uniform permeation of the liquid. Such a joining method utilizable for the analytical element of the invention is disclosed in EP 0 226 465A.

The second fibrous porous layer is utilized as a spreading layer of the liquid sample spotted on the analytical element, and it has preferably a metering action. The metering action is such that a sample spotted on the spreading layer spreads at a substantially uniform amount per unit area in lateral directions without uneven distribution of any component in the sample. The spreading layer may contain a hydrophilic polymer or surfactant as disclosed in EP 0 162 301A and Japanese Patent KOKAI 63-219397, 63-112999 and 62-182652 in order to adjust the spreading area, spreading speed and the like. The second fibrous porous layer is laminated to the nonfibrous porous layer by an adhesive in the same manner as described for the first and second nonfibrous layers.

The void volume per unit area of the first fibrous porous layer may be equal to or different from the nonfibrous porous layer. The void volume per unit area of the nonfibrous porous layer may also be equal to or different from the second fibrous porous layer. Each void volume can be changed by controlling the void content or the thickness.

Light-reflective particles, such as titanium dioxide or barium sulfate, may be dispersed in the first fibrous porous layer using a hydrophilic polymer as a binder. By incorporating the light-reflective particles, when the optically detectable change, such as the coloring or the color change produced in the registration layer, the reagent layer or the like is measured by reflection photometry from the side of the light-transmissive support, the first fibrous porous layer can shield the red color of the hemoglobin contained in the erythrocyte of the whole blood sample. It can also function as a light-reflecting layer or background layer. Preferable binders are gelatin, gelatin derivatives, polyacrylamide and the like. Light-reflective particulates may also be incorporated into either or both of the nonfibrous porous layer and the nonporous reagent layer described hereafter.

Preferable materials for the light-transmissive water-impermeable support are polyethylene terephthalate, polystyrene and cellulose esters, such as, cellulose triacetate. In order to bind the layer laminated to the support securely, the support is usually provided with an undercoating layer or is made hydrophilic.

The analytical element of the invention may employ various layer constructions as referred to in the disclosures of U.S. Pat. Nos. 3,992,158, 4,292,272 and EP 0 226 465A. The following embodiments are practically employable as the analytical element of the invention:

(1) The second fibrous porous layer, the nonfibrous porous layer, the first fibrous porous layer and the support, superposed in this order.

(2) The second fibrous porous layer, the nonfibrous porous layer, the first fibrous porous layer, an adhesive layer (or a water-absorption layer) and the support, superposed in this order.

(3) The second fibrous porous layer, the nonfibrous porous layer, the first fibrous porous layer, a registration layer and the support, superposed in this order.

(4) The second fibrous porous layer, the nonfibrous porous layer, the first fibrous porous layer, a reagent layer and the support, superposed in this order.

(5) The second fibrous porous layer, the nonfibrous porous layer, the first fibrous porous layer, a nonporous reagent layer, a registration layer and the support, superposed in this order.

The support may include a superposed subbing layer. The registration layer is, in general, the layer where the dye produced in the presence of an analyte diffuses and is optically detected there through the light-transmissive support. The registration layer may be composed of a hydrophilic polymer, and it may contain a mordant, for example, a cationic polymer in the case where the dye is anionic. The water-absorption layer is, in general, the layer where the dye produced in the presence of an analyte does not diffuse into it substantially, and it may be composed of a hydrophilic polymer which is readily swellable.

The reagent layer, the registration layer, the water-absorption layer or the like may be composed of a hydrophilic polymer. The hydrophilic polymer includes gelatin, its derivatives, such as phthalated gelatin, cellulose derivatives, such as hydroxymethyl cellulose, agarose, polyacrylamide, polymethacrylamide and copolymers of acrylamide or methacrylamide and various vinyl monomers.

One or more nonfibrous or fibrous porous layers may be incorporated between the first or second fibrous porous layer and the nonfibrous porous layer. A barrier layer, a light-reflecting layer or the like may be incorporated between the reagent layer and the first fibrous porous layer or between the registration layer and the first fibrous porous layer. An adhesive layer for binding the first fibrous porous layer may be provided on the support, the subbing layer, the water-absorption layer, the registration layer or the like. The adhesive layer is preferably composed of a hydrophilic polymer capable of binding the porous layer, when it is wet with water to swell, such as, gelatin, gelatin derivatives, polyacrylamide and starch.

The reagent composition includes the compositions capable of producing an optically detectable substance such as a dye in the presence of an analyte. Examples of the reagent composition include the compositions producing a dye by the oxidation of a leuco dye, such as, triarylimidazole leuco dyes disclosed in U.S. Pat. No. 4,089,747 and diarylimidazole leuco dyes disclosed in EP 0 122 641A, etc., the compositions containing a diazonium salt, compositions containing a chromogenic compound capable of being coupled to a coupler by oxidation to produce a dye, such as, combinations of 4-aminoantipyrines (chromogenic compound) and phenols or naphthols (coupler) and compositions comprising a dye precursor compound capable of producing a dye in the presence of a coenzyme in reduced form and an electron carrier. In the case of analytical elements for measuring an enzyme activity, the reagent composition may be comprised of a self-color developing type substrate capable of releasing a color material, such as, p-nitrophenol or p-nitrophenyl phosphate. The reagent composition may also contain an enzyme; the examples being described in the specification of EP 0 226 465A from page 5 to page 7.

The reagent composition may contain an activator, a buffer, a hardening agent, a surfactant and the like. The buffers suitable for the analytical element of the invention are carbonate buffers, borate buffers, phosphate buffers, Good's buffers, and the like. Such a buffer may be selected with reference to "Tanpakushitsu Koso no Kiso-Jikken-Ho (Fundamental Experimental Method of Proteins, Enzymes)" (Horio et al., Nanko-Do, 1981), Biochemistry, vol. 5, No. 2 pp 467–477, 1966, or the like.

To incorporate a nonporous reagent layer between the first fibrous porous layer and the support is preferred. The nonporous reagent layer is a substantially nonporous uniform layer composed of a hydrophilic polymer as a binder. Preferable binders are gelatin, its derivatives, such as, phthalated gelatin, cellulose derivatives, such as, hydroxymethyl cellulose, agarose, polyacrylamide, polymethacrylamide and copolymers of acrylamide or methacrylamide and various vinyl monomers, and the like. The nonporous reagent layer contains at least a part of a reagent composition capable of producing an optically detectable change in the presence of an analyte. The whole or most of the reagent composition may be incorporated into the nonporous reagent layer, or separated into the nonporous reagent layer and the first fibrous porous layer.

When the nonporous reagent layer is absent, at least a part of the reagent composition is incorporated into one of the aforementioned three porous layers. All components of the reagent composition may be incorporated into a single porous layer, such as the first fibrous layer, or they may be divided and incorporated into two or more porous layers. In addition, a part of the components of the reagent composition may be incorporated into the aforementioned layer containing the hydrophilic polymer as a binder. While, when the nonporous reagent layer is present, at least a part of the reagent composition must be incorporated therein. All components of the reagent composition may be incorporated into the nonporous reagent layer, or they may be divided and incorporated into two or more layers, such as, the porous layers and the layers containing the hydrophilic polymer as a binder. In the latter case, to incorporate the whole or most of the reagent composition into the nonporous reagent layer and the first fibrous porous layer is preferred. When the reagent composition contains a self-color-developing type substrate, the substrate is incorporated into the porous reagent layer, the first fibrous porous layer or the nonfibrous porous layer.

As the method for incorporating the reagent composition into at least one of the three porous layer, the reagent composition is dissolved or suspended in water or an organic solvent, and immersed into or applied onto the porous layer. Then, the porous layer is bound to another water-permeable layer, such as a reagent layer, for example, by the method disclosed in U.S. Pat. No. 4,292,272. In this method, the whole surface of a layer containing a hydrophilic polymer binder, such as a binding layer or a reagent layer is almost uniformly moistened with water or the water containing a surfactant, and the porous layer is superposed thereon. Then, it is laminated with light uniform pressure. Instead, the porous layer is first bound to another water-permeable layer, such as an undercoating layer, a binding layer or a water-absorption layer, and thereafter, the solution or suspension of the reagent composition is applied onto the porous layer. The coating method and the immersing method may be conventional, and the coating method may be selected from dip coating, doctor coating, hopper coating, curtain coating and the like. When a layer containing the reagent composition and a hydrophilic polymer as a binder is coated on the support or the like followed by binding the first nonfibrous porous layer which does not contain the reagent composition thereon by the method disclosed in U.S. Pat. No. 4,292,272 or the like, the reagent composition can substantially be incorporated into the first nonfibrous porous layer.

The analytical element of the invention is particularly effective for the quantitative analysis of the macromolecular components in whole blood, such as total protein, albumin and various enzymes, the components bound to protein, such as bilirubin, and the hydrophobic components, such as cholesterol and glycerides as well as the lower molecular components, such as glucose, urea, uric acid and creatinine. The analytical element can also be used for determining the presence of an antigen or an antibody by an immunological method through incorporation of an appropriate antigen or an antibody into one or more of the porous layers.

By using the analytical element of the invention, the analytical values of various analytes free from the hematocrit values of blood samples can be obtained from whole blood samples and blood plasma samples in the range of the hematocrit values of 0% to 55%.

EXAMPLES

Example 1 Analytical Slide for the Determination of Total Cholesterol 1-1 Preparation of Leuco Dye Emulsion

| The following leuco dye solution was prepared. | |
| --- | --- |
| 2-(4-hydroxy-3,5-dimethoxyphenyl)-4-[4-(dimethylamino)phenyl]-5-phenethylimidazole acetate | 5.7 g |
| 2-(4-hydroxy-3,5-dimethoxyphenyl)-4-[4-(dimethylamino)phenyl]-5-phenethylimidazole hydrochloride | 0.8 g |
| N,N-diethyllaurylamide | 104 g |
| The following gelatin solution was prepared. | |
| Alkali-treated gelatin | 300 g |
| Water | 1900 g |
| Bis[(vinylsulfonylmethylcarbonyl)amino]methane | 3.0 g |

The gelatin solution was stirred by an emulsifier "TK Auto Homomixer", Tokushu Kikai Kogyo K. K.) at about 5,700 rpm, and the leuco dye solution was added. The mixture was stirred for about 30 minutes to obtain the emulsion.

1-2 Coating of Dye-Forming Reagent Layer

The above emulsion was applied onto a gelatin-subbed transparent polyethylene terephthalate (PET) sheet (support) 180 μm in thickness at a rate of 150 g/m² and dried to form a dye-forming non-porous reagent layer (dry coverage about 26 g/m²).

1-3 Lamination of First Fibrous Porous Layer

The surface of the dye-forming reagenr layer was moistened uniformly with about 30 g/m² of water at 25° C. A tricot fabric about 250 μm thick knitted from 50 deniers PET spun yarn by 36 gauge was superposed thereon, and dried to laminate the fabric to the dye-forming reagent layer.

Subsequently, the following composition was applied onto the tricot fabric, and dried to obtain a first fibrous porous layer.

| Methyl cellulose | 3.0 g/m² |
| --- | --- |
| Titanium dioxide (Mean particle size: 0.3 μm) | 24 g/m² |
| Lipoprotein lipase | 2,000 IU/m² |
| Cholesterol esterase | 2,500 IU/m² |
| Cholestrol oxidase | 2,500 IU/m² |
| Peroxidase | 2,500 IU/m² |
| Potassium dihydrogen phosphate | 7.3 g/m² |
| Potassium ferrocyanide | 0.7 g/m² |

1-4 Impregnation of Second Fibrous Porous layer

A tricot fabric about 250 μm thick knitted from 50 deniers PET spun yarn by 36 gauge was immersed in the following aqueous solution to fill the void portions with the solution, and taken out followed by drying to obtain a second fibrous porous layer.

| Polyethylene glycol (Molecular weight: 50,000) | 2.0 g |
| --- | --- |

| -continued | |
| --- | --- |
| Sodium tetraborate | 2.0 g |
| Pure water | 96 g |

1-5 Lamination of Second Porous Layer and Spreading Layer

The impregnated tricot fabric was heated to 80° C., and hot melt type adhesive melted at 130° C. was adhered to the surface of the tricot fabric in a dot-shaped by pattern transferring from a gravure roll utilizing the gravure printing. Each dot was a circle having a diameter of 0.3 mm, and the distance between each center of the dots was 0.6 mm. The area of the dots was about 20%, and the adhered hot melt type adhesive was about 3 g/m². A cellulose acetate membrane filter ("MICROFILTER FM 300", manufactured by Fuji Photo Film Co., Ltd.) having an effective pore size of 3 μm, a thickness of 140 μm and a void content of about 80% was used as the nonfibrous porous layer. The nonglossy side of the membrane filter was immediately faced to the tricot fabric, and both were joined through the dot-shaped adhesive by passing a laminating roller.

1-6 Completion of Analytical Element

The laminate was laminated to the first porous layer in a similar manner to the above method. That is, a hot melt type adhesive was adhered in a dot-shaped pattern to the membrane filter face of the above laminate by transferring from a gravure roll utilizing the gravure printing, and immediately faced to the face of the first fibrous porous layer, and joined by the dot-shaped adhesive by passing a laminating roller.

Thus, an integral multilayer analytical element for the quantitative analysis of total cholesterol was completed. The analytical element consisted of a support, a dye-forming reagent layer, a first fibrous porous layer, a nonfibrous porous layer and a second fibrous porous layer laminated in this order. The second fibrous porous layer and the nonfibrous porous layer act as the blood cell-separating layer cooperatively. The first fibrous porous layer acts as a reaction layer to produce ferric ion in the presence of cholesterol. In the dye-forming reagent layer, a dye is produced by the ferric ion produced in the first fibrous porous layer, and the dye is optically measured through the transparent support.

1-7 Preparation of Analytical Slide

The analytical element was cut into square pieces having a side of 15 mm, and placed in a slide frame described in Japanese Patent KOKAI No. 57-63452 to complete an analytical slide for the quantitative analysis of total cholesterol.

Comparative Example 1

An analytical slide for the quantitative analysis of total cholesterol was prepared in the same manner as Example 1, except that a cellulose acetate membrane filter ("MICROFILTER FM 300", manufactured by Fuji Photo Film Co., Ltd.) having an effective pore size of 1.2 μm, a thickness of 140 μm and a void content of about 80% was used instead of the tricot fabric used as the first fibrous porus layer in Example 1. The glossy face was faced to the dye-forming non-porous reagent layer.

Measuring Example 1

The effect of hematocrit value of blood samples upon both of the above analytical slides were measured. A human blood plasma sample containing 145 mg/dl of total cholesterol and a human whole blood sample having the same content of total cholesterol and a hematocrit value of 25%, 40% or 55% were used. Each 20 μm sample were spotted to the second fibrous porous layers of the analytical slide of Example 1 and of Comparative Example 1, and incubated at 37° C. for 3 minutes and 6 minutes. Then, the reflection optical density of the respective analytical slides were measured by using a light having a central wave length of 640 nm from the PET support side. The results are shown in Table 1.

TABLE 1

| Hematocrit Value | Example 1 | Comparative Example 1 |
|---|---|---|
| 0% (Plasma) | 0.598 | 1.068 |
| 25% | 0.604 | 0.945 |
| 40% | 0.609 | 0.851 |
| 55% | 0.599 | 0.768 |

As shown in Table 1, in the case of the analytical slide of Example 1, similar reflection optical densities were obtained irrespective of the hematocrit value in the range of 0% (plasma) through 55%. Whereas, in the case of the analytical slide of Comparative Example 1, the reflection optical density was sharply reduced with the increase of the hematocrit value.

Measuring Example 2

The dependency of the analytical slide of Example 1 on total cholesterol concentration was measured. Eight human whole blood samples containing a total cholesterol concentration in the range of 63 to 319 mg/dl and a hematocrit value in the range of 19 to 44% were used.

A 20 μl sample was spotted to the second fibrous porous layer of the analytical slide of Example 1, and incubated at 37° C. for 6 minutes. Then, the reflection optical density of respective analytical slides was measured by using a light having a central wave length of 640 nm from the PET support side. The results are shown in Table 2 and FIG. 1. The sample of 0 mg/dl total cholesterol concentration was a saline solution.

TABLE 2

| Cholesterol Concentration (mg/dl) | Hematocrit Value (%) | Optical Density |
|---|---|---|
| 0 | 0 | 0.145 |
| 63 | 29 | 0.378 |
| 100 | 28 | 0.495 |
| 106 | 19 | 0.524 |
| 148 | 36 | 0.603 |
| 165 | 32 | 0.662 |
| 245 | 44 | 0.810 |
| 274 | 38 | 0.827 |
| 319 | 42 | 0.915 |

The measured results of Table 2 plotted in FIG. 1 indicates that the optical density has a definite relation to the total cholesterol concentration of blood samples irrespective of their hematocrit values.

Removal of Blood Cells in Analytical Element

The removal ability of blood cells from whole blood was examined as to the analytical slide of Example 1 and Comparative Example 1. 20 μl of samples whole blood having a hematocrit value of 40% were spotted to the second fibrous porous layer of the analytical slide of Example 1 and Comparative Example 1, and kept at 35° C. for 6 minutes. Each layer of both analytical elements was separated, and the reflection optical density of the upper surface and the lower surface of the respective layers were measured by using a light having a central wave length of 640 nm. The results are shown in Table 3. The numerical values in Table 3 are the remainders obtained by the subtraction of the reflection optical density of the corresponding face when none was spotted to the analytical elements as a blank therefrom.

TABLE 3

| | Example 1 | Comparative Example 1 |
|---|---|---|
| Second Fibrous Porous Layer | | |
| Upper Surface | 0.46 | 0.48 |
| Lower Surface | 0.47 | 0.47 |
| Nonfibrous Porous Layer | | |
| Upper Surface | 0.53 | 0.46 |
| Lower Surface | 0.82 | 0.73 |
| First Fibrous Porous Layer Upper Surface | 0.00 | 0.19 |

As shown in Table 3, in the case of the analytical slide of Example 1, the blood cell components were entirely removed from the whole blood upper layers than rather in the first fibrous porous layer.

Example 2

2-1 Coating of Dye-forming Reagent Layer

The following aqueous solution was applied onto a gelatin-subbed colorless transparent smooth PET film 180 μm in thickness so that the dry thickness became 15 μm (156 cc/m²), and dried to form a dye-forming reagent layer.

| | |
|---|---|
| Gelatin | 190 g |
| Surfactant (p-Nonylphenoxypolyglycidol, Olin) (containing 10 glycidol units on the average) | 8 g |
| Peroxidase | 150,000 IU |
| FAD | 240 mg |
| TPP | 1000 mg |
| Pyruvate oxidase | 150,000 IU |
| Dye* | 3.0 g |
| Water | 1360 g |
| Adjusted to pH 6.5 with dil. NaOH. | |

Dye:
2-(3,5-dimethoxy-4-hydroxyphenyl)-4-phenethyl-5-(4-dimethylaminophenyl)imidazole 2-2 Coating of Adhesive Layer The following aqueous solution was applied onto the above reagent layer so that the dry thickness became 3 μm (60 cc/m²), and dried to form an adhesive layer.

| | |
|---|---|
| Gelatin | 40 g |
| Surfactant (p-Nonylphenoxypolyglycidol, Olin) (containing 10 glycidol units on the average) | 1.6 g |
| Water | 600 g |
| Adjusted to pH 7.0 with dil. NaOH. | |

2-3 Lamination of First Fibrous Porous Layer

The surface of the adhesive layer was moistened uniformly with about 30 g/m² of water at 25° C., and a polyester broadcloth having a void volume of 9.8 μl/m² was laminated thereto with a light pressing followed by drying.

Subsequently, the following composition was applied onto the broadcloth at a rate of 100 cc/m², and dried to form a first fibrous porous layer.

| | |
|---|---|
| Tris(hydroxymethyl)aminomethane | 2.2 g |
| Potassium monophosphate | 4.5 g |
| Sodium α-Ketoglutarate | 4.0 g |

-continued

| | |
|---|---|
| L-Alanine | 27.5 g |
| Hydroxypropylmethyl cellulose | 8.7 g |
| ("Metholose 90 SH 100", Shinethus Chemical) Containing 28 to 30% of methoxy group and 7 to 12% of hydroxypropoxy group. The viscosity of 2% aqueous solution was 50 cps at 20° C. | |
| Dye(4,4'-monomethine-bis[1-(p-sulfophenyl)-3-methyl-5-pyrazolone]oxonol) | 0.7 g |
| Surfactant (p-octylphenoxypolyethoxyethanol) (containing 10 ethoxy unit on the average) | 27 g |
| Titanium dioxide (rutile type) | 70 g |
| Magnesium chloride | 2.4 g |
| Water | 880 g |
| Adjusted to pH 7.5 with dil. NaOH. | |

2-4 Impregnation of Second Fibrous Porous Layer

A tricot fabric about 250 μm thick knitted from 50 deniers PET spun yarn by 36 gauge was immersed in the following aqueous solution to fill the void portions with the solution, and taken out followed by drying to obtain a second fibrous porous layer.

| | |
|---|---|
| Polyethylene glycol (Molecular weight: 50,000) | 2.0 g |
| Sodium tetraborate | 2.0 g |
| Purified Water | 96 g |

2-5 Lamination of Second Porous Layer and Spreading Layer

The impregnated tricot fabric was heated at 80° C., and hot melt type adhesive melted at 130° C. was adhered to the surface of the tricot fabric in a dot-shaped by pattern transferring from a gravure roll utilizing the gravure printing. Each dot was a circle having a diameter of 0.3 mm, and the distance between each center of the dots was 0.6 mm. The area of the dots was about 20%, and the adhered hot melt type adhesive was about 3 g/m². A cellulose acetate membrane filter ("MICROFILTER FM 300", manufactured by Fuji Photo Film Co., Ltd.) having an effective pore size of 3 μm, a thickness of 140 μm and a void content of about 80% was used as the nonfibrous porous layer. The nonglossy side of the membrane filter was immediately faced to the tricot fabric, and both were joined through the dot-shaped adhesive by passing a laminating roller.

2-6 Completion of Analytical Element

The laminate was laminated to the first porous layer in a similar manner to the above method. That is, a hot melt type adhesive was adhered in a dot-shaped pattern to the membrane filter face of the above laminate by transferring from a gravure roll utilizing the gravure printing, and immediately faced to the face of the first fibrous porous layer, and joining through the dot-shaped adhesive by passing a laminating roller.

Thus, an integral multilayer analytical element for measuring alanine aminotransferase (ALT) activity is produced. The analytical element consists of a support, a dye-forming reagent layer, a first fibrous porous layer, a nonfibrous porous layer and a second fibrous porous layer laminated in this order. The second fibrous porous layer and the nonfibrous porous layer act as the blood cell-separating layer cooperatively. The first fibrous porous layer acts as a reaction layer to produce pyruvic acid in the presence of ALT. The dye-forming reagent layer acts as a layer to convert the pyruvic acid produced in the first fibrous porous layer into a dye through hydrogen peroxide, and the dye is optically measured through the transparent support.

2-7 Preparation of Analytical Slide

The analytical element was cut into square pieces having a side of 15 mm, and placed in a slide frame described in Japanese Patent KOKAI No. 57-63452 to complete an analytical slide for measuring ALT activity.

Measuring Example 3

The analytical slide for measuring ALT activity was evaluated as follows. A human whole blood sample was centrifuged and a suitable amount of the blood plasma was mixed with the blood cell portion to prepare whole blood samples having a hematocrit value of 25%, 40% or 55%. Prior to the above mixing, a part of the plasma was replaced by an ALT solution prepared by adding ALT to 7% human serum albumin (HSA) aqueous solution so that the whole blood samples had an ALT activity of 800 units/l. As to the blood plasma sample, a part was replaced by the ALT solution so as to have the same ALT activity.

20 μl samples of the whole blood were spotted to the second fibrous porous layer of the analytical slide of Example 2, and kept at 37° C. in a sealed vessel, and the reflection optical density was measured at a wave length of 640 nm from 2.5 minutes to 4 minutes after the spotting to determine the variation rate per second of optical density. The results are shown in Table 4.

TABLE 4

| Hematocrit Value (%) | Variation Rate of Optical Density (per sec.) |
|---|---|
| 0 | $3.92 \times 10^{-4}$ |
| 25 | $3.78 \times 10^{-4}$ |
| 40 | $3.93 \times 10^{-4}$ |
| 55 | $3.69 \times 10^{-4}$ |

As shown in Table 4, in the case of the analytical slide of Example 2, an almost constant variation rate of optical density was obtained in the hematocrit value from 0% (plasma) to 55%, irrespective of the hematocrit value.

Measuring Example 4

The dependency of the analytical slide of Example 2 on ALT activity was measured. Various amounts of ALT were added to 7% HSA aqueous solution to prepare ALT solutions in 7% HSA. A whole human blood sample was centrifuged, a suitable amount of the blood plasma was replaced by the ALT solution, and the mixture was mixed again with the blood cell portion to obtain whole blood samples having a hematocrit value of 40% and various ALT activities. 20 μl samples of the whole blood were spotted to the second fibrous porous layer of the analytical slide of Example 2, and kept at 37° C. in a sealed vessel, and the reflection optical density was measured at a wave length of 640 nm from 2.5 minutes to 4 minutes after the spotting to determine the variation rate per second of optical density. The results are shown in Table 5 and FIG. 2. The data shown in the last line of Table 5 was of the original whole blood prior to the centrifugation.

TABLE 5

| ALT Activity (units/l) | Variation Rate of Optical Density (per sec.) | Hematocrit Value (%) |
|---|---|---|
| 24 | 0.005 | 40% |
| 72 | 0.317 | " |
| 121 | 0.545 | " |

TABLE 5-continued

| ALT Activity (units/l) | Variation Rate of Optical Density (per sec.) | Hematocrit Value (%) |
|---|---|---|
| 220 | 1.126 | " |
| 361 | 1.693 | " |
| 618 | 2.753 | " |
| 624 | 3.079 | " |
| 795 | 3.843 | " |
| 959 | 4.542 | " |
| 1714 | 7.384 | " |
| 538 | 2.345 | 47% |

Figure 2:
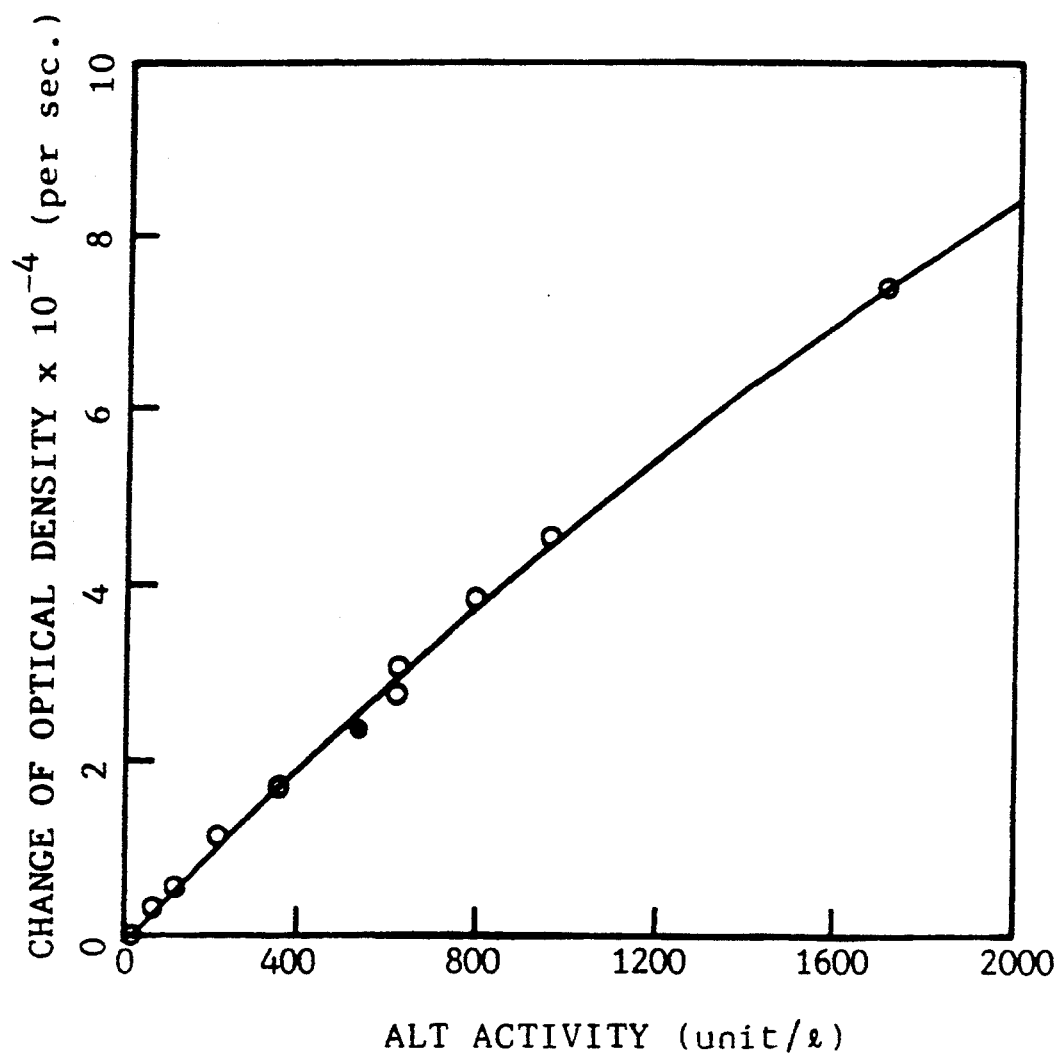
FIG. 2 is a graph indicating a relation between ALT activity of whole blood samples and a reflection optical density of multilayer analytical elements.

FIG. 2 wherein the data shown in Table 5 were plotted indicates substantially linear relationship between the ALT activity and the variation rate optical density.

We claim:

1. An integral multilayer analytical element which comprises a first fibrous porous layer, a nonfibrous porous layer of a membrane filter composed of a blushed polymer prepared by a phase separation method, a free side surface of the filter being disposed on the side facing the first fibrous porous layer, a pore size of the filter being the smallest in the vicinity of the free surface, and a second fibrous porous layer superposed in this order onto a water-impermeable light-transmissive support, the second fibrous porous layer and the nonfibrous porous layer acting as a blood cell separating layer which limits a hematocrit value of a blood sample from effecting an analysis thereof, the above three porous layers being integrally laminated to each other substantially closely by an adhesive discontinuously disposed so as to form microspaces continuing through from one layer to the next so as not to interfere with the approximately uniform permeation of liquid, and a reagent composition which produces an optically detectable change in the presence of an analyte being incorporated in at least one of said three porous layers wherein the first fibrous porous layer has a pore size which is larger than the pore size of the nonfibrous porous layer.

2. The analytical element of claim 1 wherein said reagent composition is incorporated in the first fibrous porous layer.

3. An integral multilayer analytical element which comprises a nonporous reagent layer, a first fibrous porous layer, a nonfibrous porous layer of a membrane filter composed of a blushed polymer prepared by a phase separation method, a free side surface of the filter being disposed on the side facing the first fibrous porous layer, a pore size of the filter being the smallest in the vicinity of the free surface, and a second fibrous porous layer superposed in this order onto a water-impermeable light-transmissive support, the second fibrous porous layer and the nonfibrous porous layer acting as a blood cell separating layer which limits a hematocrit value of a blood sample from effecting an analysis thereof, the nonporous reagent layer containing a hydrophilic polymer as a binder, the above three porous layers being integrally laminated to each other substantially closely by an adhesive discontinuously disposed so as to form microspaces continuing through from one layer to the next so as not to interfere with the approximately uniform permeation of liquid, and a reagent composition which produces an optically detectable change in the presence of an analyte being incorporated at least in said nonporous reagent layer, wherein the first fibrous porous layer has a pore size which is larger than the pore size of the nonfibrous porous layer.

4. The analytical element of claim 3 wherein said reagent composition is incorporated in the nonporous reagent layer and the first fibrous porous layer.

5. The analytical element of claim 3 wherein substantially the whole reagent composition is incorporated in the nonporous reagent layer.

* * * * *